United States Patent [19]
Landrum et al.

[11] Patent Number: 5,976,822
[45] Date of Patent: Nov. 2, 1999

[54] METHOD AND REAGENT FOR MONITORING APOPTOSIS AND DISTINGUISHING APOPTOSIS FROM NECROSIS

[75] Inventors: Eileen Landrum, Miami; Adry Galiounghi, Miami Lakes; Nancy Garcia, Miami; Ursino Del Valle, Hialeah; Frank J. Lucas, Boca Raton, all of Fla.

[73] Assignee: Coulter International Corp., Miami, Fla.

[21] Appl. No.: 08/915,414

[22] Filed: Aug. 20, 1997

Related U.S. Application Data

[63] Continuation-in-part of application No. 08/444,051, May 18, 1995, Pat. No. 5,698,411.

[51] Int. Cl.⁶ .............................. C12Q 1/37; C12Q 1/00
[52] U.S. Cl. .............................. 435/23; 435/24; 435/4; 435/968; 435/29; 435/34
[58] Field of Search ............................ 435/23, 24, 4, 435/968, 29, 34

[56] References Cited

U.S. PATENT DOCUMENTS 4,557,862 12/1985 Mangel et al. ............................ 435/23
4,640,893 2/1987 Mangel et al. ............................ 435/23
5,698,411 12/1997 Lucas et al. ............................. 435/29

OTHER PUBLICATIONS

Alnemri, E., et al., "Human ICE/CED–3 Protease Nomenclature," *Cell*, vol. 87, p. 171, 1996.

Enari, M., et al., "Sequential Activation of ICE–like and CPP32–like Proteases during FAS–Mediated Apoptosis," *Nature*, vol. 380, pp. 723–726, Apr. 25, 1996.

Gross, E., eds. *The Peptides: Analysis, Synthesis, Biology*, vol. 3, pp. 3–99, Academic Press, 1981.

Duque, R.E., "Flow Cytometric Analysis of Lymphomas and Acute Leukemias," Ann. NYAS, *Clinical Flow Cytometry*, 677, pp. 309–325, Mar. 20, 1993.

*Primary Examiner*—Louise N. Leary
*Attorney, Agent, or Firm*—Mitchell E. Alter

[57] ABSTRACT

The ability to determine the stage or pathway of cysteine proteases in a single cell assay has long been desired as a material event in apoptosis. The present invention relates to a method and assay reagents for determining enzyme activity and relating said activity to the apoptotic pathway. In addition, the method find utility in distinguishing apoptotic activity from necrotic activity.

20 Claims, 6 Drawing Sheets

FIG. 1A

SAMPLE
(Leukocytes)

⇓

WASH 4X
> 10,000: 1

⇓

ADD
REAGENT
INCUBATE

⇓

LYSE
UNWANTED
CELLS

⇓

DATA
COLLECTION

⇓

RESULT

FIG. 1B

SAMPLE
(Leukocytes)

⇓

LYSE
UNWANTED
CELLS

⇓

WASH 4X

⇓

ADD
REAGENT
INCUBATE

⇓

DATA
COLLECTION

⇓

RESULT

FIG. 1C

SAMPLE
(Platelets,
RBCs &
Leukocytes)

⇓

WASH 4X

⇓

ADD
REAGENT
INCUBATE

⇓

DATA
COLLECTION

⇓

RESULT

FIG. 1D

SAMPLE
(Platelets or
RBCs or
Lymph, Mono,
Gran)

⇓

MECHANICAL
SEPARATION
OF CELL
POPULATION

⇓

WASH 4X

⇓

ADD
REAGENT
INCUBATE

⇓

DATA
COLLECTION

⇓

RESULT

FIG. 4
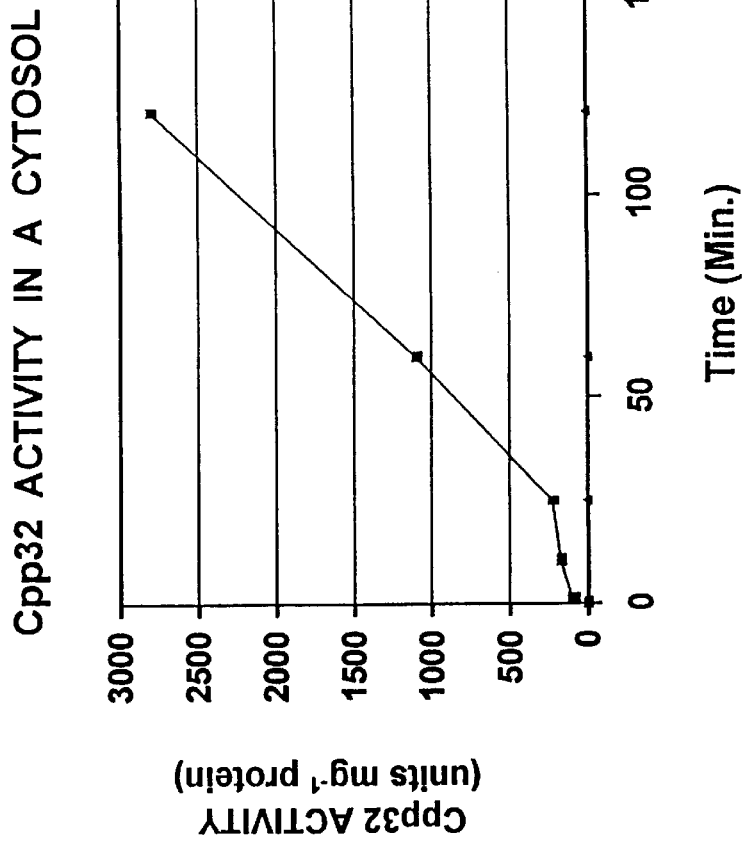
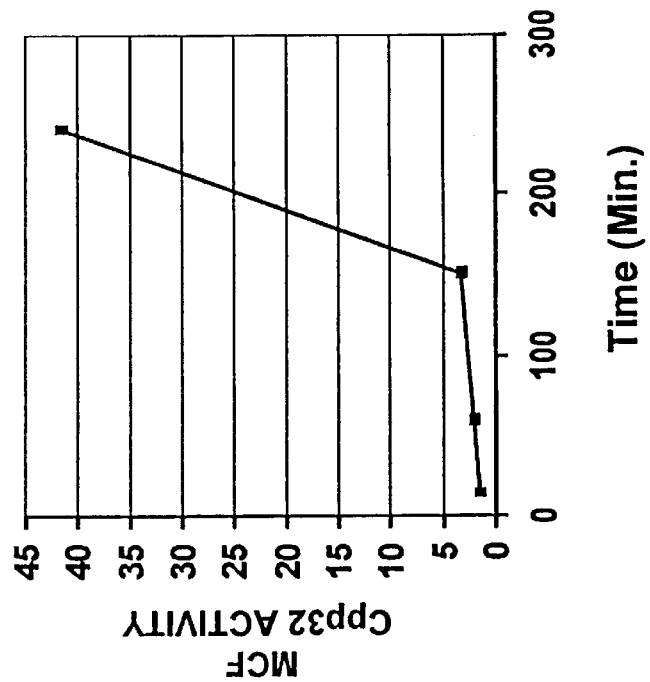

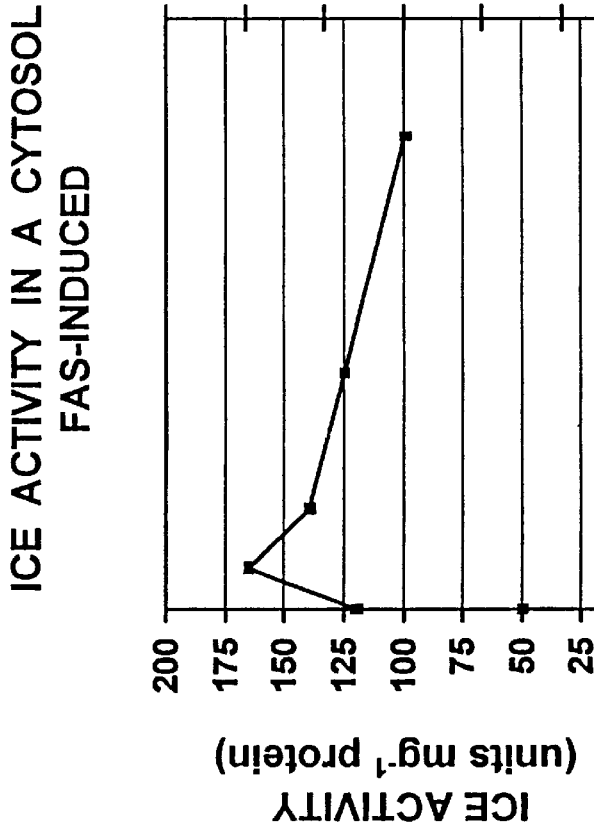
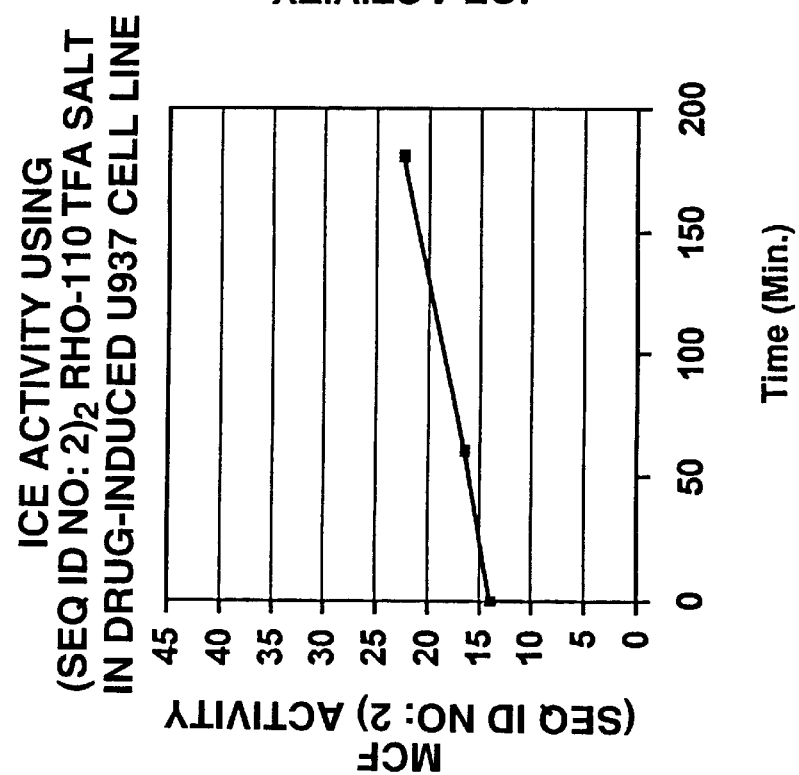
FIG. 5

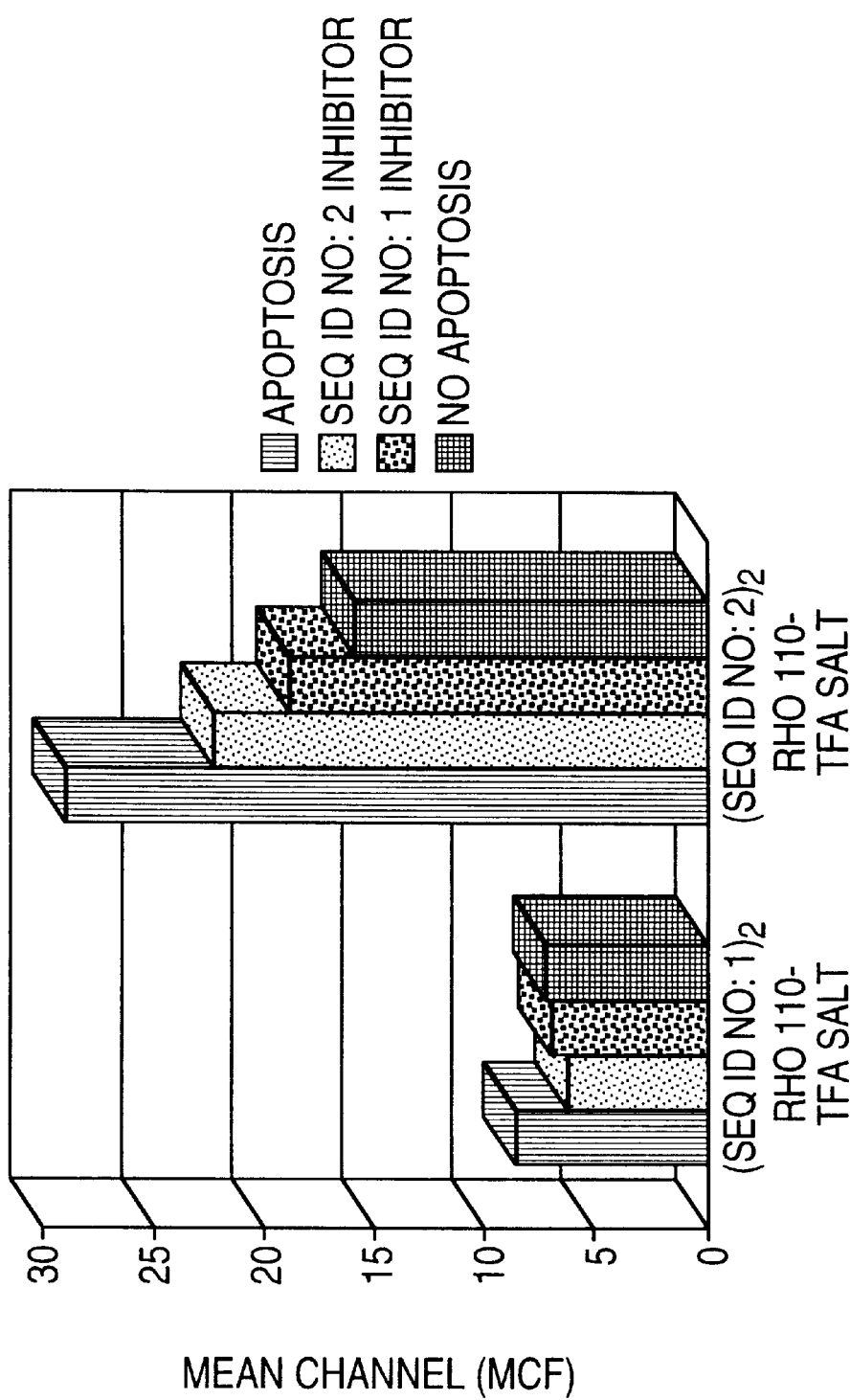

METHOD AND REAGENT FOR MONITORING APOPTOSIS AND DISTINGUISHING APOPTOSIS FROM NECROSIS

CROSS REFERENCE TO RELATED APPLICATION

This application is a continuation-in-part of co-pending patent application Ser. No. 08/444,051, filed May 18, 1995.

BACKGROUND OF THE INVENTION

1. Technical Field of the Invention

This invention relates generally to cytoenzymology, and more particularly to methods and reagents used in cytoenzymology.

2. Discussion of the Background Art

Apoptosis, or programmed cell death, is a process that involves the activation of a genetic program when cells are no longer needed or have become seriously damaged. This process, occurring in most cells from higher eukaryotes, is necessary for normal development and maintenance of homeostasis. It is a major defense mechanism of the body, getting rid of unwanted and possibly dangerous cells such as virus-infected cells, tumor cells, and self-reactive lymphocytes. Apoptosis probably exists as a safeguard to prevent damaged cells from reproducing. If the damaged cells remained, they may ultimately be detrimental to the organism.

Apoptosis involves a cascade of specific biochemical events. Regulation of apoptosis involves a large number of genes. These can be classified into three general categories. The first is made up of genes whose primary function is to suppress apoptosis. This group includes some members of the bcl-2 family. Other members of the bcl-2 family can promote apoptosis. The second group includes the intermediate genes upstream such as Fas/Fas ligand, myc, p53, and WAF1. The last group includes genes that act as effectors of apoptosis. An example is the interleukin-1β converting enzyme (ICE) family of genes.

Fas is a cell surface protein that triggers apoptosis in a variety of cell types. The Fas death pathway can be triggered by either anti-Fas monoclonal antibody or by cell-associated Fas ligand. This protein is identical to the CD95 protein. CD95 is involved in regulation of tissue development and homeostasis. Cloning of Fas and APO-1 cDNA has demonstrated that these two genes are identical. The Fas antigen is a cell surface protein that belongs to the tumor necrosis factor/nerve growth factor receptor family. The mechanism by which Fas triggers cell death is not completely understood. It appears to require multivalent cross-linking of the receptor. This inhibits RNA and protein synthesis in certain cell types. The amino acid sequences that take part in cell death have been mapped in Fas and tumor necrosis factor receptors. This area is called the "death domain" and is essential for the initiation of apoptosis, which may happen through an interaction with other intracellular proteins.

Many cysteine proteases have been identified in mammals. Interleukin-1β-converting enzyme (ICE) is a cysteine protease whose activity is increased in apoptosis. Several homologues of ICE have been identified, including CPP32- and Ich-1-like proteases. Specific inhibitors of ICE-like proteases can inhibit apoptosis. This indicates there is a requirement for specific degradation by proteases in mammalian apoptosis. The ICE family of cysteine proteases has an indispensable role in the regulation of apoptosis.

It appears that the ICE family of proteases process themselves and each other by proteolytically cleaving a "pre" enzyme into the active form. The ICE family of proteases is generically referred to as caspase enzymes. Alnemri, et al., *Cell*, Volume 87, page 171, 1996. The "c" is intended to reflect a cysteine protease mechanism and "aspase" refers to their ability to cleave after aspartic acid, the most distinctive catalytic feature of this protease family.

Enari, et al, *Nature* 380, pages 723–726 (1996) have suggested that apoptotic events may sequentially activate ICE and CPP32-like proteases in Fas-mediated apoptosis. Enari used specific inhibitors of ICE and CPP32 to show that CPP32-inhibitor only inhibited CPP32 activity. ICE-inhibitor, on the other hand, inhibited both ICE and CPP32 activity. This indicates that the production of CPP-32-like activity during Fas-mediated apoptosis depends on the previous presence of ICE-like activity. This experiment was performed in a cytosol of approximately a billion human cells.

Cell death can occur by either necrosis or apoptosis. Necrosis, which is not genetically controlled, is usually the result of physical injury. Apoptosis is genetically controlled and is the deliberate cellular response to specific environmental and developmental stimuli. The signs of necrosis and apoptosis are different. Necrosis involves the destruction of cytoplasmic organelles and a loss of plasma membrane integrity. Cells undergoing apoptosis exhibit cell shrinkage, membrane blebbing, chromatin condensation and fragmentation. After the DNA damage in the caspase enzyme pathway, there are a series of events which occur that involve calcium activation and calpain enzymes which further leads to other cellular changes and regulation of cytoplasmic enzymes.

A major difference between necrosis and apoptosis in vivo is the complete elimination of the apoptotic cell before an inflammatory response is seen. Necrosis usually causes inflammation. Thus, apoptosis can be thought of as a clean and neat process where cells are killed with minimal damage to surrounding cells or tissue.

One test to study proteases is to provide a substrate that is recognized by the enzyme, with a fluorescent compound which will undergo a detectable change when the substrate, or "leaving group", is cleaved from the compound by the enzyme. Mangel et al., U.S. Pat. Nos. 4,557,862 and 4,640,893, disclose Rhodamine 110-based derivatives as fluorogenic substrates for proteinases. These compounds have the general formula:

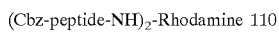

$$(\text{Cbz-peptide-NH})_2\text{-Rhodamine 110}$$

where the peptide includes known amino acids or amino acid derivatives, and "Cbz" refers to the blocking group benzyloxycarbonyl. When the amino groups of Rhodamine 110 are blocked the compound is "quenched", and is relatively colorless and non-fluorescent. Cleavage of one of the peptides from the non-fluorescent bisamide substrate results in a 3500-fold increase in fluorescence intensity.

Other substrates for conducting cytoenzymological studies are sold by Kamiya Biomedical Company, Seattle Washington and have the formula (Z-Asp Glu Val Asp-AFC), (Z-Ala Ala Asp-AFC) and (Z-Tyr-Val-Ala-Asp-AFC), wherein AFC is 7-amino4 trifluoromethyl coumarin and Asp Glu Val Asp, Ala Ala Asp and Tyr-Val-Ala-Asp are abbreviations for amino acids as later defined in this specification. However, these reagents either bind to the external cell membrane or exhibits solubility problems so that they fail to measure intracellular enzymes. In addition, courmarin excite and emits in the ultraviolet light range which is known to cause DNA damage which is detrimental to cell viability.

Prior method and reagents have failed to provide an effective test to monitor the efficacy of a drug or the progression of a disease through the use of an intracellular analysis of apoptosis. Moreover, the present invention provides an additional feature of distinguishing between apoptosis and necrosis by using enzymes other than the ICE family of caspase enzymes.

SUMMARY OF THE INVENTION

In view of the foregoing, an object of the present invention is to provide an assay reagent for determining the activity of an enzyme in a metabolically active whole cell, said assay reagent comprising at least one water soluble physiologically acceptable salt having the ability to pass through a cell membrane, said assay compound having an unblocked leaving group selected for cleavage by an enzyme to be analyzed selected from cysteine protease, dipeptyl peptidase and calpain, and a fluorogenic indicator group being selected for its ability to have a non-fluorescent first state when joined to the leaving group, and a fluorescent second state excitable at a wavelength above 450 nm when the unblocked leaving group is cleaved from the indicator group by the enzyme, wherein said fluorogenic indicator group is selected from the group consisting of rhodamine 110, rhodol, fluorescein and derivative thereof; said assay reagent having a fluorescence less than the auto-fluorescence of a metabolically active cell.

Another object of the present invention is to provide a method of performing an assay for detecting the presence of a enzymatic activity in a metabolically active whole cell to determine the apoptotic stage of the cell. The method comprises contacting a test, metabolically active whole cell with an assay reagent, said assay reagent comprising at least one water soluble physiologically acceptable salt having the ability to pass through a cell membrane, said assay compound having an unblocked leaving group selected for cleavage by an enzyme to be analyzed selected from cysteine protease, dipeptyl peptidase and calpain, and a fluorogenic indicator group be ing selected for its ability to have a non-fluorescent first state when joined to the leaving group, and a fluorescent second state excitable at a wavelength above 450 nm when the unblocked leaving group is cleaved from the indicator group by the enzyme, wherein said fluorogenic indicator group is selected from the group consisting of rhodamine 110, rhodol, fluorescein and deriva-tive thereof, s aid assay reagent having a fluorescence less than the auto-fluorescence of a metabolically active cell; sensing for said fluorescent second state of the indicator group for the test, metabolically active whole cell to produce a test result; and determining an apoptotic stage of said metabolically active whole cell from said test result.

As will be more fully appreciated from the ensuing Detailed Description of Preferred Embodiments, the present invention is particularly advantageous in determining the stage or pathway of apoptosis. In addition, the method find utility in distinguishing apoptotic activity from necrotic activity.

BRIEF DESCRIPTION OF THE DRAWINGS

There are shown in the drawings embodiments which are presently preferred, it being understood, however, that the invention is not limited to the precise instrumentalities and arrangement s shown, wherein:

FIGS. 1A, 1B, 1C and 1D are flow charts of four assay protocols accord ing to the invention;

FIG. 4 is a graphical depiction of a reagent of this invention when tested in a metabolically active cell compared to a prior art reagent in a cytosol in a receptor mediated system.

FIG. 5 is a graphical depiction of a reagent of this invention when tested in a metabolically active cell compared to a prior art reagent in a cytosol.

FIG. 6 is an apoptosis inhibition study of U937 cells preincubated with ac-(SEQ ID NO:1)-CHO and ac-(SEQ ID NO:2)-CHO.

DETAILED DESCRIPTION OF THE PREFERRED EMBODIMENTS

Figure 2:
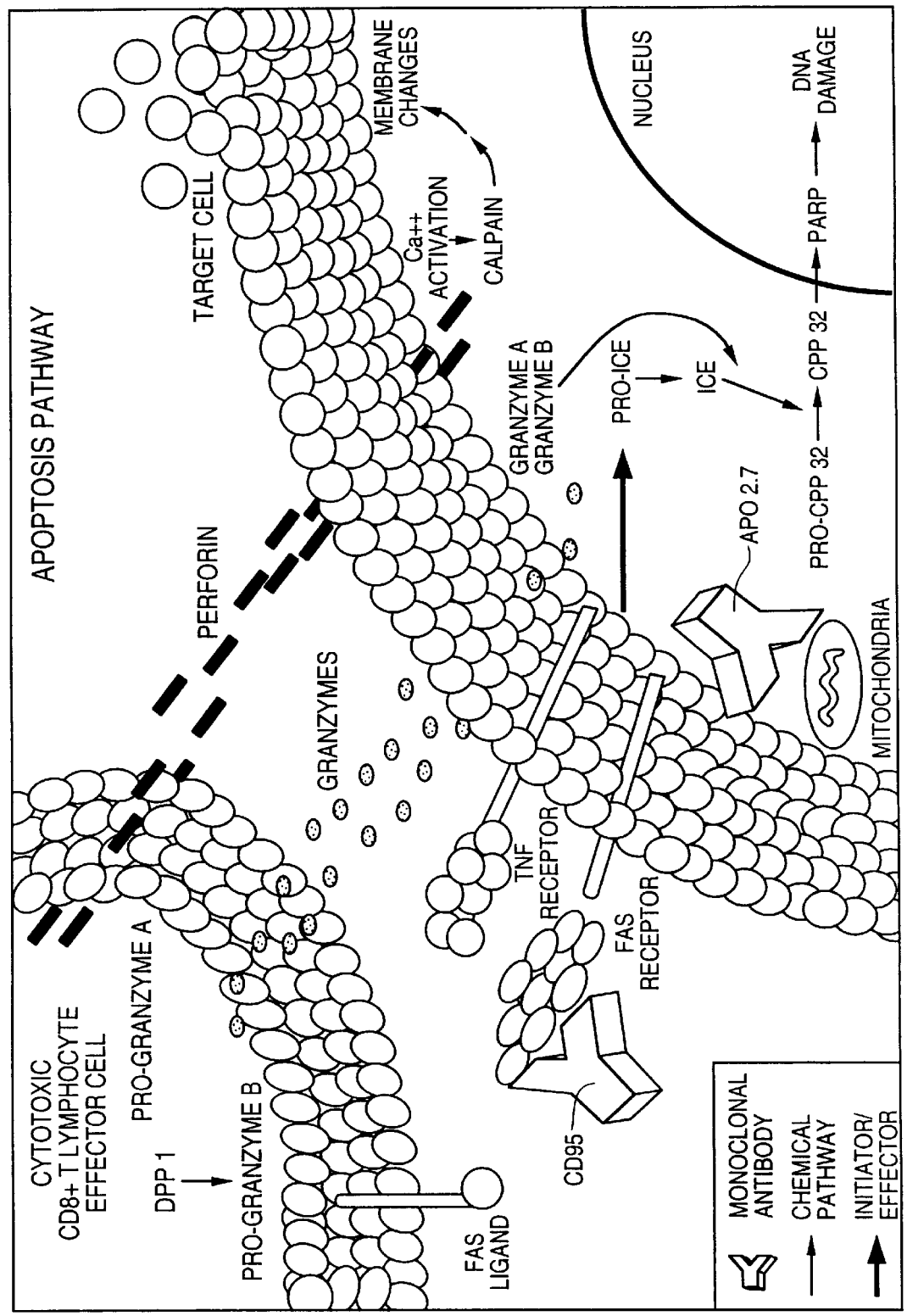
FIG. 2 is a graphical description of the apoptosis pathway.

The following outline will be used to describe the preferred embodiments of this invention:
I. Types of Assays
II. Preparation of Metabolically Active Whole Cells
III. Assay Compound
IV. Preparation Of An Assay Reagent Which Contains An Assay Compound
V. Assay Conditions
VI. Assay Protocol
VII. Data Analysis
I. Types of Assays It has been discovered that the assay reagent can be used to measure enzymatic activity of a metabolically active whole cell to provide an indication of the progress of a disease or the efficacy of a drug by determining the apoptotic stage or pathway in said metabolically active whole cell. More specifically, it has been found that the activity of one or more enzymes changes with disease progression. Changes in the activity of one or more enzymes can be examined to provide an indication of the presence and progress of a disease. In addition, the measurement of the activity of certain enzymes can provide an indication of the response to certain drugs or treatments, since the activity of one or more enzymes will change if the drug is successfully fighting, modulating or treating the disease.

An enzymatic assay is performed by contacting metabolically active cell with an assay reagent. The assay reagent contains an indicator group and an unblocked leaving group. The leaving group is selected for cleavage from the indicator group by a targeted enzyme. The reaction occurs for a period of time sufficient for the leaving group to be cleaved from the indicator group by the targeted enzyme. Sensing for one or more reaction states confirms cleavage of the indicator group by the enzyme.

There are at least two methods to perform the assay of the present invention 1) performing a single assay and detecting a difference between the beginning state and the end state of a substrate, such as the cleavage of a single substrate by a target enzyme to yield free peptide and fluorescent indicator dye to determine the apoptotic state or pathway; and 2) performing a series of assays with several substrates to differentiate between necrosis and apoptosis.

II. Preparation of Metabolically Active Whole Cell Sample

The assay reagent is reacted with a metabolically active whole cell analyte. The metabolically active whole cells are contained in tissue, blood, cell cultures or other cell containing constituents, such as in spinal fluid, peritoneal, or a tissue cell suspension, prepared from bone marrow aspirates or lymph nodes such as from a biopsy. In a preferred embodiment, the metabolically active whole cells are obtained from whole blood or bone marrow aspirates. Preferably, the metabolically active whole cells are separated into cell types. The metabolically active cells to be analyzed are isolated by known techniques such as differential lysis, differential centrifugation, and affinity columns. However, separation of the cells to be studied from other cells is not always essential.

The cells are usually washed to remove any extracellular enzymes, optionally with lysis or physical separation of unwanted cells. Several preferred techniques for accomplishing this are summarized in FIGS. 1A–1D.

The analysis of the segregated metabolically active cells provides specificity for a particular enzyme analysis. For example, when the metabolically active cell is a leukocyte blood cell, the method comprises separating the leukocyte cell from the cell analyte, washing the remaining leukocyte cell to remove any serum or plasma enzymes, contacting an assay reagent compound with the leukocyte cell, and determining fluorescence from the leukocyte cell (See FIG. 1B). A modification of this method comprises washing the cell analyte to remove any serum or plasma enzymes, contacting an assay compound with the cell analyte, separating the leukocyte blood cells from the cell analyte, and determining fluorescence from the leukocyte cells (See FIG. 1A). In addition, another method that can be used for cell analytes of leukocyte blood cells, nucleated erythrocyte blood cells and platelets analytes comprises washing the cell analyte to remove any serum or plasma enzymes, contacting an assay compound with the analyte and determining fluorescence from the analyte (See FIG. 1C).

The assay of the present invention is particularly useful for measuring intracellular concentrations of enzymes in mammalian cells such as human cells. However, the assay should also be useful in various or other types of cells which have metabolic activity.

III. Assay Compound

According to the present invention, an assay reagent is manufactured for determining the activity of an enzyme in a metabolically active whole cell. The assay reagent must be compatible with the cell such that the cell will remain metabolically active for at least the duration of the assay.

The assay reagent comprises at least one assay compound which is capable of passing through the cell wall. The assay compound must be small enough that it can be transmitted into the cell. An assay compound having a molecular weight of less than about 5,000 is presently preferred.

The assay compound contains a leaving group and an indicator group. The leaving group is selected for cleavage by the enzyme to be analyzed. The indicator group is selected for its ability to have a first state when joined to the leaving group, and a second state when the leaving group is cleaved from the indicator group by the enzyme. The indicator group is preferably excitable (caused to fluoresce) at a wavelength about the visible range, for example, at wavelength between about 450 to 500 nanometers (nm). The indicator group will usually emit in the range of about 480 to 620 nm, preferably 500 to 600 nm and more preferably 500 to 550 nm. Auto-fluorescence of the cell is most prevalent below about 500 nm.

The indicator group is preferably derived from fluorogenic compounds. The indicator group should be quenched when joined to the leaving group. The term quenched means that the indicator group has almost no fluorescence when joined to the leaving group. When the leaving group is separated from the indicator group, the resulting indicator compound will have a fluorescence.

Suitable fluorogenic indicator compounds include xanthine compounds. Preferably, the indicator compounds are rhodamine 110; rhodol; and fluorescein.

In addition, derivatives of these compounds which have the 4' or 5' carbon protected are acceptable indicator compounds. Preferred examples of the derivative compounds include 4'(5')thiofluorescein, 4'(5')-aminofluorescein, 4'(5')-carboxyfluorescein, 4'(5')-chlorofluorescein, 4'(5')-methylfluorescein, 4'(5')-sulfofluorescein, 4'(5')-aminorhodol, 4'(5')-carboxyrhodol, 4'(5')-chlororhodol, 4'(5')-methylrhodol, 4'(5')-sulforhodol; 4'(5')-aminorhodamine 110, 4'(5')-carboxyrhodamine 110, 4'(5')-chlororhodamine 110, 4'(5')-methylrhodamine 110, 4'(5')-sulforhodamine 110 and 4'(5')thiorhodamine 110. "4'(5')" means that at the 4' or 5' position the hydrogen atom on the carbon atom is substituted with a specific organic group or groups as previously listed.

The leaving group is selected according to the enzyme that is to be assayed. The leaving group will have utility for assaying many kinds of cellular enzymes, including proteases and esterases. As will be discussed herein, the assay compounds are particularly useful for detecting intracellular enzymes in living cells. The leaving group is selected from amino acids, peptides, esters and mixtures thereof. Suitable leaving groups for protease enzymes are preferably prepared by the synthesis of amides of Asp Glu Val Asp (SEQ ID NO:1), Tyr-Val-Ala-Asp (SEQ ID NO:2), Ala Ala Asp (SEQ ID NO:3), Val Glu lie Asp (SEQ ID NO:4) and Pro Phe Arg (SEQ ID NO:5). Suitable leaving groups for an esterase enzymes are preferably prepared by the synthesis of carboxylic acids esters of SEQ ID NO:1, SEQ ID NO:2, SEQ ID NO:3, SEQ ID NO:4 and SEQ ID NO:5. Other leaving groups suitable for the enzyme to be assayed can be determined empirically or obtained from the literature.

It has been discovered that when the leaving group is a salt, it will significantly improve the transmission of the assay compound into the cell. The selection of an appropriate salt requires a consideration of the compatibility with the cell, solubility in the aqueous media, and cleavage by the enzyme. Particular care is required in the selection of the peptide salt since even isoenzymes have been found to be specific in their recognition of particular salts.

The assay compound is purified to acceptable levels for the assay. It is very important that the side reaction products, by-products and starting materials from the synthesis of the assay compound be removed which would diminish the utility of the assay. Non-physiologically acceptable impurities should be removed. In addition, the background noise generated from impurities should be less than the autofluorescence of a metabolically active cell.

IV. Preparation Of An Assay Reagent Which Contains An Assay Compound

Protecting groups are preferably employed when synthesizing the leaving group to prevent undesired side reactions of the leaving group during synthesis of the assay compound. N-terminal protecting groups and polar organic protecting groups on the other portion of the amino acid molecule are used to prevent undesired side reactions of the amino acids during syntheses of the peptides. The protecting groups, also known as blocking groups, are removed prior to the assay, unless the presence of a particular blocking group or groups is found not to interfere with the assay.

The N-terminal protecting groups include an arylcarbonyl, alkylcarbonyl, alkoxycarbonyl, aryloxycarbonyl, aralkoxycarbonyl, arylsulfonyl, alkylsulfonyl, or other equivalents known to those skilled in the art of peptide syntheses. The polar organic groups hydroxyl, guanidinyl, sulfhydryl and carboxyl or other equivalents should be chemically protected as known to those skilled in the art of peptide syntheses. Gross and Meienhofer, eds., *The Peptide*, 3(3–81) (Academic Press, New York, 1981), describe numerous suitable amine protecting groups.

Preferred examples of the N-terminal blocking groups include formyl, acetyl, trifluoroacetyl, benzyloxycarbonyl, phthaloyl, benzoyl, acetoacetyl, chloroacetyl, phenoxycarbonyl, carbobenzoxy, substituted benzyloxycarbonyl, tertiarybutyloxycarbonyl, isopropyloxycarbonyl, allyloxycarbonyl, phthaloyl, benzoyl, acetoacetyl, chloroacetyl, phenoxycarbonyl, methoxysuccinyl, succinyl, 2,4-dinitrophenol, dansyl, p-methoxybenzenesulfonyl, and phenylthio.

A compound containing a blocking group and a leaving group such as an amino acid is reacted with an agent to form an active intermediate complex. The leaving group is selected based on the leaving group desired in the final assay compound. Suitable agents are known to those skilled in the art of peptide chemistry. Examples of suitable agents include carbodiimides, preferably 1-ethyl-3-(3'-dimethylaminopropylcarbodiimide hydrochloride) and benzotriazolyl-N-oxy-tris(dimethylamino)phosphonium hexafluorophosphate (BOP reagent) and 1-hydroxybenzotriazole (HOBT reagent). The reagents are typically stirred in a flask at room temperature. The chemical structure of the intermediate complex is presently unknown. The presence of the complex can be confirmed by thin layer chromatography.

The intermediate complex is further reacted with a compound containing an indicator group (indicator compound) to form a reaction product. As appreciated by those skilled in the art of peptide chemistry, the indicator compound is dissolved in a solvent to facilitate the reaction with the intermediate complex. The reagents are typically stirred in a flask at room temperature for a time sufficient to form a reaction product. The reaction product can be confirmed by developing a thin layer chromatography (TLC) plate in an organic solvent. The reaction product should be a non-fluorescent compound. When the indicator group is rhodamine 110, rhodol or a derivative, the presence of the reaction product is confirmed by contacting the reaction product with an acidic solution, such as hydrochloric acid, which cleaves the leaving group thereby forming a colored product. When the indicator group is fluorescein or a derivative, the presence of the reaction product is confirmed by contacting the reaction product with a basic solution, such as sodium hydroxide, which cleaves the leaving group thereby forming a colored product. If only one spot on the TLC plate gives a positive test and there are no trace amounts of fluorescence, the reaction product is of acceptable purity for this stage of the process.

The reaction product is then separated from other side reaction products, by-products and starting materials in the following manner. Preferably, the reaction product is concentrated to an oil under reduced pressure so as to remove volatile solvents that might be present. The reaction product oil is then redissolved in a minimum amount of an organic solvent, preferably chloroform, methylene chloride, and further separated from the other side reaction products, by-products and starting materials by normal phase preparative high pressure liquid chromatography (HPLC). Other conventional methods of separation can be employed. Separation of the reaction product is verified by TLC, as previously described, and analytical reverse phase HPLC. The reverse phase HPLC will depict the presence of one major band of reaction product.

The reaction product is separated from the other side reaction products, by-products and starting materials so that the reaction product can be further processed by having the blocking groups removed. If the reaction product is not sufficiently separated from the other side reaction products, by-products and starting materials, then a low yield of the assay compound containing an indicator group and leaving group will be obtained. Moreover, the quality of the separation will have an effect on the amount of purification that will be subsequently necessary to obtain an assay compound for use in the metabolically active cell.

The blocking group which is blocking (protecting) the leaving group is then removed from the reaction product to obtain an assay compound ("intermediate compound" is formed at this step if the final assay compound is a salt) which contains an indicator group and a leaving group. The reactions are conducted to obtain a free amino acid xanthine derivative by methods known to those skilled in the art. When the blocking group on the indicator group comprises benzyloxycarbonyl (CBZ), the blocking group is removed by a catalytic reaction of the reaction product in an organic solvent with hydrogen in the presence of palladium or platinum. When the blocking group on the indicator group comprises 9-fluorenylmethyloxycarbonyl (FMOC), the blocking group is typically removed by the reaction of the reaction product in a polar solvent with an organic base. Further details of this process are shown in Example 1.

To confirm that the blocking group has been removed and the resulting intermediate compound has formed, the intermediate compound is analyzed by analytical reverse phase HPLC. In addition, the resulting intermediate compound can be further confirmed by developing a thin layer chromatography plate in an organic solvent.

This intermediate compound having an indicator group and leaving group is then reacted with an acid or a base to form an assay compound, which is a physiologically acceptable salt. It is important according to the method of the invention that the assay compounds be physiologically acceptable to the cell. The selection of the acid or base has a material affect on whether the resulting assay compound will be physiologically acceptable to the cell. In addition, it has been found that the selection of the acid affects the selectivity of the assay compound for the enzyme to be assayed. It has been found that hydrogen bromide (HBr), even when buffered, kills cells.

Preferably the acid that is used to form the salt is selected from the group consisting of hydrochloric, sulfuric, nitric, maleic, acetic, trifluoroacetic, tartaric acid, citric, succinic and p-toluenesulfonic acid. More preferably the acid is selected from the group consisting of acetic, trifluoroacetic, tartaric acid, and p-toluenesulfonic acid. Most preferably the acid is trifluoroacetic. When a base is used, ammonia or organic bases can be used. Most preferably, the base is ammonia.

The assay compound is purified, preferably by reverse phase HPLC. It is very important that the side reaction products, by-products and starting materials from the synthesis of the assay compound be removed which would diminish the utility of the assay. Non-physiologically acceptable impurities should be removed. In addition, the background noise generated from impurities should be less than the auto-fluorescence of a metabolically active cell.

It has been found that when a leaving group is present as an impurity, the leaving group can be an inhibitor to enzyme activity. Still further, metal impurities in any of the starting materials can poison the enzymes, prevent hydrolysis of the assay compound and interfere with the accuracy of the enzyme assay.

In addition, impurities will create background fluorescence which will add to the natural fluorescence of the cell to create a level of background noise which can interfere with the detection of enzyme generated fluorescence. Fluorescent impurities can be taken up by the cell, and a rate measurement of fluorescence against time will show a false rate of increasing fluorescence that is due only to this cellular uptake of fluorescent impurities. This is a particular problem if the assay is conducted to determine the presence or absence of an enzyme, since this impurity will indicate a rate of fluorescence which will falsely appear to be attributable to enzymatic activity.

The assay compound can be purified by techniques known in the art. As shown in Example 1, the purification of rhodamine 110 substrate can be accomplished by reverse phase column chromatography. In the case of the preparation of salts of peptide-rhodamine 110 compounds, a significant level of impurities is created. These impurities include free indicator compound, monosubstituted rhodamine 110, blocked amino acids and peptides.

The fluorescence impurities should be removed to a level that they do not obscure the baseline detection of the enzyme in the cell. The baseline detection can be established by analyzing log dilutions of an indicator group. Preferably the impurities should be removed so that the fluorescence of the impurities is less than the auto-fluorescence of the metabolically active cell.

Assays for peptidases using assay compounds generate fluorescence generally in the range of $10^{-5}$ to $10^{-6}$ Molar free rhodamine 110.

Therefore, it is preferred that the free rhodamine 110 and blocked peptide impurities in the assay reagent should be removed to a concentration of less than the fluorescence generated by about $1 \times 10^{-6}$M and more preferably less than the fluorescence generated by about $10^{-7}$ Molar free indicator group. This amounts to a 100,000 photon count using rhodamine 110 as a standard at $10^{-7}$–$10^{-8}$M, preferably $5 \times 10^{-8}$M in a 1 cm path length cuvette when measured over 10 min. on a photon counting spectrofluorometer manufactured by the SLM Company of Chicago, Ill. This corresponds to a use level on the flow cytometer where no cellular false positive can be detected for a 10 minute period at the highest sensitivity setting. In the case of the peptide-rhodamine 110 compounds, this has been found to require a concentration of impurities of less than one part per one hundred thousand, more preferably less than one part per five hundred thousand, most preferably less than one part per million.

The presence of impurities causes a decrease in the storage stability of the compound, resulting in an increased autohydrolysis which leads to increased background fluorescence. A compound should be free of impurities such that when the compound (or reagent containing the compound) is stored at 4° C. for 30 days, preferably 90 days, more preferably 180 days, most preferably one year, the background fluorescence increases less than 10%, preferably less than 5%, most preferably less than 1% over these time periods, respectively. The purified compound or lyophilized reagent are stored in a sealed container over dry nitrogen under atmospheric pressure. The starting point in time for measuring stability is usually immediately after purification of the assay compound is completed but it can be any time such as immediately after the preparation of the assay reagent is completed.

Normal phase preparative HPLC procedures are presently preferred to separate peptide-indicator compound from the impurities. As is known in the art, solvents of varying polarity can be mixed in varying concentrations in order to more effectively separate the peptide-indicator compound from the various impurities. Thin layer chromatography (TLC) can be utilized to test for the presence of the rhodamine 110 substrate in the eluate. This is done by placing a drop of the eluent on the TLC plate, and then treating the spot with a suitable acid, such as HCl, to detect the presence of the rhodamine 110 substrate, which will turn bright yellow when treated with acid. Analytical reverse phase high pressure liquid chromatography is used to test the peptide-indicator product for purity, as evidenced by a single sharp band in the absorption spectrum.

The assay reagent must be compatible with the metabolically active cell. The assay reagent should have an osmolality of from about 250 milliosmoles to 350 milliosmoles, preferably from about 275 milliosmoles to 320 milliosmoles. In addition, the pH of the assay reagent will be between about 4.0 and 9.5, preferably between about 5.0 and 8.0. For the caspase enzymes it has been found that the most preferred pH is between about 6.8 to 8.0. For granzymes, which are a specific cysteine protease, the most preferred pH is between 7.0 to 8.5.

It has been further found that the efficacy of an intracellular assay is substantially improved by the addition of one or more components in the assay reagent. Examples of improvements include a reduction of reaction time, increased selectivity for the targeted enzyme, reduction of competing enzyme reactions, increasing signal of enzyme reaction, increasing reactivity of the assayed enzyme relative to other non-targeted enzymes, increasing the retention time of the indicator group within the cell and other similar advantageous results.

Additional components include buffers, cofactors, modulators, inhibitors, activators for increasing activity of the target enzymes over other non-targeted enzymes, solubilizing components and retention components can be included in the assay reagent to improve the enzyme assay results. These components are physiologically acceptable to the metabolically active whole cell that is being assayed.

The chemical nature of the buffer is important to the reactivity of the assay compound with the cellular enzymes. Buffer components that show no inhibitory effect to the cells can be used. Suitable buffer components are Hanks balanced salt, tris-glycine, HEPES, glycine sodium hydroxide, TRIS-base (TRIS[hydroxy methyl]amino methane), and cacodylate. The preferred buffer components are MES for acidic solutions, Hanks for neutral solutions, and glycine sodium hydroxide for basic solutions.

Cofactors are components not consumed in the enzymatic reactions, but are required to make the enzyme function. Suitable cofactors include metals such as $Ca^{+2}$, $Zn^{+2}$, $Mg^{+2}$, $Mn^{+2}$ and halogens, such as $Cl^{-1}$. These cofactors can increase the selectivity of the enzyme for the leaving group. The cofactors can also be co-enzymes or vitamins.

Inhibitors and poisons (or toxins) are components that can be added to reduce the activity of non-targeted enzymes that provide competing reactions for the leaving group. Inhibitors are usually very selective for a particular enzyme. For example, Bestatin is a specific inhibitor for amino peptidases which will cohydrolyze the leaving groups.

The assay compound must be soluble in the aqueous media. Solubility is measured by light scatter using the percent transmittance of light (or absorbance) through the mixture of the media and assay compound. As measured on a spectrophotometer, the assay compound should have a background color at a concentration to be used in an assay of less than 1000, preferably less than 800, and most preferably less than 500 milliabsorbance units at 340 nanometers (25° C.) blanked against distilled or deionized water. The assay compound will usually be used at a concentration of 0.5 to 10 mM. A useful concentration for determining solubility is 5 mM.

Preferably, a two fold excess quantity of the assay compound that will react with the enzyme during the time of the assay must be soluble in the aqueous media. An excess of assay compound is preferred. If an insufficient amount of the assay compound is provided, the enzyme reaction will completely hydrolyze the assay compound and the dynamic range of the assay will be limited. The resulting indicator compound will have a limited fluorescence duration. However, when an excess of the assay compound is employed, the enzyme reaction will continuously hydrolyze the assay compound and the fluorescence duration will continue during the enzyme reaction. This provides the advantage of having a longer time period in which to sense for one or more reaction states of the assay compound.

The media in which the assay compound is dissolved must be compatible with the cell so that the cell can remain metabolically active in the media for at least the duration of the assay. The media is preferably sterile and free of endotoxin and chemicals that adversely affect the physiology of the cell. The assay compound is preferably completely soluble in the media at the concentration at which it is used. The assay compound is preferably used in concentrations up to the saturation or the suspension level or before turbidity occurs. The media may be physiological saline or a buffered solution (phosphate buffered saline) in which the assay compound and other additives are dissolved. The media should preferably include a buffer agent so that the pH of the assay mixture of metabolically active cells and assay compound is maintained at a point that is appropriate for the enzyme hydrolysis.

For storage purposes the compound and media mixture should be lyophilized under conditions where sublimation of the solvent occurs upon application of a vacuum. Applying a vacuum to the sample at a temperature where a liquid forms on the solid before going to a gas phase, referred to as "melt back" may cause degradation of the compound. Appropriate temperatures should be determined for each compound, and preferred temperatures are usually −5° C. to −35° C. for predominantly aqueous solutions. During the thermal cycle of lyophilization, heat may be applied after sublimation to drive off any additional moisture. The product temperature should never exceed the heat applied and the product should be brought to room temperature over 15 to 72 hours. The vacuum should be returned to atmospheric conditions by bleeding in dry nitrogen. The product is stoppered at atmospheric pressure and temperature. The lyophilized compound is stored at 4° C. to 8° C. and may be reconstituted using endotoxin-free deionized water.

Auto-hydrolysis, which is the nonspecific hydrolysis of the substrate, yields cellular fluorescence not derived from the target enzyme. Stability of the substrate compound has been demonstrated to be a key factor in preventing auto-hydrolysis.

The assay compound and/or the assay reagent should be sufficiently stable so that no auto-fluorescence is created by the degradation of the assay compound prior to cleavage by the enzyme. Preferably, when the assay compound or assay reagent is stored at 20° C. for 30 days, preferably 90 days, more preferably 180 days and most preferably one year, the reagent exhibits a photon count of 100,000 or less. Photons can be measured by using a 2 millimolar solution of assay compound in deionized water and a path length of 1 cm against a rhodamine 110 standard as previously described. Fluorescent impurities should account for less than 10% of the fluorescence generated during the assay.

An acceptable reagent should have the following three characteristics; (1) there should be a low level of native free fluorescence that is absorbed by the cells, non-specifically. Thus, there should be a low level of fluorescent impurities such as free indicator compounds. The acceptable and preferred levels of these impurities have already been described. (2) The reagent should be stable over time so that it does not need to be used shortly after it is prepared. Certain impurities and certain reagent additives can increase the rate of autohydrolysis which increases the fluorescence of the reagent. Acceptable and preferred stabilities have already been discussed. (3) The reagent should also have a high enough rate of reaction with the enzyme being measured so that fluorescence generated as a result of reaction between the enzyme and the reagent can be easily measured. In one aspect, the reaction rate should be sufficiently high that fluorescence generated as a result of cleavage of the leaving group inside the cell is at least 2 times, preferably at least 10 times, more preferably at least 50 times and most preferably at least 100 times greater than other non-specific fluorescence generated in the assay. In another aspect, the reagent should contain an unblocked assay compound which has a reaction rate which is at least 2 times, preferably at least 5 times, more preferably at least 100 times, most preferably at least 1000 times the reaction rate of a corresponding blocked assay compound. For example, the unblocked assay compounds of the present invention which contain unblocked amino and or peptide leaving groups have an enzymatic reaction rate which is considerably greater than the reaction rate of the corresponding compound wherein the amine group(s) on the leaving group is blocked by, for example, a Cbz group.

As used herein, either individually or as part of a larger group, "alkyl" means a linear, cyclic, or branched-chain aliphatic moiety of one to 10 carbon atoms; "substituted alkyl" means an alkyl group having a substituent containing a heteroatom or heteroatoms such as N, O, or S; "aryl" means an aromatic moiety, e.g., phenyl, of 6 to 18 carbon atoms, unsubstituted or substituted with one or more alkyl, substituted alkyl, nitro, alkoxy, or halo groups; and "alkaryl" means an aryl moiety of 7 to 19 carbons having an aliphatic substituent, and optionally, other substituents such as one or more alkyl, substituted alkyl, alkoxy or amino groups. "Aralkyl" means a linear or branched-chain aliphatic moiety of six to 18 carbon atoms comprising an aryl group or groups.

The following common chemical abbreviations are used in the examples:

t-BOC=tertiarybutyloxycarbonyl
EDAC=1-ethyl-3-(3'-dimethylaminopropyl-carbodiimide)-hydrochloride
FMOC=9-fluorenylmethyloxycarbonyl
BOP=benzotriazoly-N-oxy-tris(dimethylamino)-phosphonium-hexafluorophosphate
HOBT=1-hydroxybenzotriazole
HPLC=High pressure liquid chromatography
TLC=Thin layer chromatography
V:V=Volume to volume The amino acids are abbreviated as follows:

| Amino Acid | Abbreviation |
| --- | --- |
| L-alanine | Ala |
| L-arginine | Arg |
| L-asparagine | Asn |
| L-aspartic acid | Asp |

-continued

| Amino Acid | Abbreviation |
| --- | --- |
| L-cysteine | Cys |
| L-glutamic acid | Glu |
| L-glutamine | Gln |
| glycine | Gly |
| L-histidine | His |
| L-isoleucine | Ile |
| L-leucine | Leu |
| L-lysine | Lys |
| L-methionine | Met |
| L-phenylalanine | Phe |
| L-prnline | Pro |
| L-serine | Ser |
| L-threonine | Thr |
| L-tryptophan | Trp |
| L-tyrosine | Tyr |
| L-valine | Val |

The synthesis of the assay compounds can be further understood by reference to the following Examples. It will be appreciated, however, that the invention is not limited to the described examples, and that other methods of preparation could be suitable to prepare reagents according to the invention.

EXAMPLE 1

Preparation of Monopeptide Derivative of Rhodamine 110 Employing the EDAC Procedure A 10-fold excess of a FMOC amino acid is placed into a round bottom flask containing a 50:50 pyridine-dimethylformamide solution (V:V) and stirred until a complete solution occurs. To this stirred solution is added a 12-fold excess of EDAC and the admixture is stirred for 30 minutes. A solution of rhodamine 110 dissolved in a minimum of a 50:50 pyridine-dimethylformamide (V:V) is added dropwise to the reaction solution. This addition requires 15–20 minutes and the reaction solution is allowed to stir at room temperature overnight. The solution is concentrated under reduced pressure to an oil. Wash oil with distilled water until water layer is colorless. This oil is dissolved into an appropriated organic solvent and the product is purified by normal phase HPLC, using solvents of increasing polarity (methylene chloride, 1% methanol-chloroform, 2% methanol-chloroform, etc.). The eluate containing the product is concentrated under reduced pressure affording a crystalline material and the purity and identity are checked by analytical reverse phase high pressure liquid chromatography and thin layer chromatography.

The crystalline material is treated with a 5% solution of piperidine dissolved in dimethylformamide. The reaction is stirred for 45 minutes and concentrated under reduced pressure. The resulting solid is triturated several times with pentane and then dissolved in a minimum amount of methanol and a 5-fold excess of trifluoroacetic acid is added. The solution is concentrated under reduced pressure to dryness and the resulting solid is centrifuged with cold diethyl ether until the ether triturate has a pH=7. If the monopeptide is polar, then the remaining protective group is removed by treating with a 30 to 50% trifluoroacetic acid solution in methylene chloride for four hours at room temperature. The solution is concentrated under reduced pressure to dryness and the resulting solid is centrifuged with cold diethyl ether until the ether triturate has a pH=7. A final purification of this trifluoroacetic acid substrate is effected with reverse phase HPLC, using solvents of decreasing polarity (water, acetonitrile, trifluoroacetic acid). The eluate containing the product is concentrated under reduced pressure and the aqueous solution is lyophilized. The product's purity and identity are checked by analytical reverse phase high pressure liquid chromatography, thin layer chromatography, and photon counting spectrofluorometry. The purity and stability of the product are also measured by monitoring the background fluorescence, autohydrolysis and enzymatic activity using the product as a substrate after storage of the product at 4° C. FIGS. 10A and 10B illustrate the stability and purity of a monopeptide-TFA salt derivative Proline-rhodamine 110 which was prepared by the procedure described in this Example. Stability (background fluorescence) is shown in FIG. 10A. Autohydrolysis (diamonds) and enzyme rate (squares) are shown in FIG. 10B.

EXAMPLE 2

Preparation of a Polypeptide Derivative of Rhodamine 110 Employing the HOBT-BOP Procedure A 4-fold excess of the FMOC polypeptide and a 4-fold excess of HOBT and BOP are placed into a round bottom flask containing a 0.6 millimolar solution of N-methylmorpholine in dimethylformamide and stirred for 10–15 minutes. To this solution is added dropwise a solution of the monopeptide rhodamine 110 dissolved in a minimum amount of a 0.6 millimolar solution of N-methylmorpholine in dimethylformamide. This addition requires 5–10 minutes, and the reaction is stirred at room temperature for four hours. The reaction solution is concentrated under reduced pressure to an oil. This oil is dissolved in methylene chloride and the crude product is purified by normal phase HPLC. The eluate containing the desired product is collected and concentrated under reduced pressure affording a crystalline material. The purity and identify of this material are checked by analytical reverse phase HPLC and thin layer chromatography. The FMOC blocking is removed by dissolving the solid in a 5% piperidine-dimethylformamide solution and stirred at room temperature for one hour. The solution is concentrated under reduced pressure, and the resulting solid is triturated several times with pentane or diethyl ether to remove the FMOC polymer. The remaining solid is dissolved in a minimum of methanol and a 5-fold excess of trifluoroacetic acid is added. The solution is concentrated under reduced pressure and the resulting solid is centrifuged with cold diethyl ether until the ether triturate has a pH=7. If the polypeptide is polar then the remaining protective group(s) is removed by treating with a 30 to 50% trifluoroacetic acid solution in methylene chloride for four hours at room temperature. The solution is concentrated under reduced pressure to dryness, and the resulting solid is centrifuged with cold diethyl ether until the ether triturate has a pH=7. A final purification of this trifluoroacetic acid substrate is effected with reverse phase HPLC. The eluate containing the product is concentrated under reduced pressure and the aqueous solution is lyophilized. The product's purity and identify are checked by analytical reverse phase HPLC, thin layer chromatography and photon counting spectrofluorometry.

EXAMPLE 3

Preparation of a Polypeptide Derivative of Rhodamine 110 (SEQ ID NO:2)$_2$ Rho 110·2TFA A 3-fold molar excess each of the FMOC-Tyr (tBu) Val Ala-polypeptide, BOP, and HOBT are dissolved in a solution of 0.6N N-methylmorpholine/DMF in a around bottom flask, and stirred for 15 minutes. To this solution is added dropwise for 5–10 minutes, a solution of the monopeptide rhodamine 110 dissolved in a minimum amount of 0.6N N-methylmorpholine/DMF. The solution is stirred at room temperature for four hours. The solvents are removed by rotoevaporation at less than 35° C., using a vacuum pump with a dry ice trap. The crude gel concentrate is dissolved in 2% MeOH/CHCl$_3$, and purified by normal phase HPLC. The eluate containing the desired product is rotoevaporated to dryness under vacuum, yielding a solid which is checked for purity by TLC, and by analytical reverse phase HPLC. The FMOC protecting group is removed by treatment with a solution of 5% (v/v) piperidine/DMF, stirring at room temperature for 1 hour. Solvents are removed by rotoevaporation under vacuum, and the resulting solid is triturated and washed with pentane several times to remove most of the FMOC polymer. The polypeptide side chain protecting groups are removed by treatment with a solution of 30–50% (v/v) TFA/CH$_2$Cl$_2$ for 4 hours at room temperature. The solution is rotoevaporated to a gel, redissolved in CH$_2$Cl$_2$ and rotoevaporated. This is repeated several times after which the solid is triturated with cold diethyl ether and centrifuged. The ether is decanted and the centrifugation is repeated until the pH of the ether is approximately 7. Finally the product is purified by reverse phase HPLC; the eluate containing the product is rotoevaporated under vacuum to remove the organic solvent and the residual aqueous solution is lyophilized. Purity is checked by analytical reverse phase HPLC and photon counting spectrofluorometry.

EXAMPLE 4

Preparation of a Polypeptide Derivative of Fluorescein (SEQ ID NO:3)$_2$ Fluorescein-2TFA A 3-fold molar excess of the BOC-polypeptide, dichlorohyexyl carbodiimide (DCC), and HOBT are dissolved in a solution of (1:1) pyridine:DMF in a round bottom flask, and stirred for 30 minutes. To this solution is added dropwise for 5–10 minutes, a solution of fluorescein dissolved in a minimum amount of (1:1) pyridine:DMF. The solution is stirred at room temperature for 18–20 hours. The solvents are removed by rotoevaporation at less than 35° C., using a vacuum pump with a dry ice trap. The crude gel concentrate is dissolved in 2% MeOH/CHCl$_3$, and purified by normal phase HPLC. The eluate containing the desired product is rotoevaporated to dryness under vacuum, yielding a solid which is checked for purity by TLC, and by analytical reverse phase HPLC. The BOC protecting group, as well as butyl side chain protecting groups present are removed by treatment with a solution of 30–50% TFA/CH$_2$Cl$_2$ for 2–6 hours at room temperature. The solution is rotoevaporated to a gel, redissolved in CH$_2$Cl$_2$ and rotoevaporated. This is repeated several times after which the solid is triturated with cold diethyl ether and centrifuged. The ether is decanted and the centrifugation is repeated until the pH of the ether is approximately 7. Finally the product is purified by reverse phase HPLC; the eluate containing the product is rotoevaporated under vacuum to remove the organic solvent and the residual aqueous solution is lyophilized. Purity is checked by analytical reverse phase HPLC and photon counting spectrofluorometry.

V. Assay Conditions

The concentration of cells to be analyzed which are contained in a media should be high enough to provide a reading of the desired number of cells within the desired time period, taking into consideration the speed of the instrument that is being used. For current flow cytometry techniques, a concentration of about three million cells per milliliter is appropriate to yield a measurement of about 10,000–15,000 cells in about 1–2 minutes.

The assay compound is generally employed in concentrations in excess of the amount which can be completely hydrolyzed by the quantity of enzyme within the time of the assay. An assay compound concentration that is too high can have a negative effect on enzyme activity.

The assay compound concentration in a cellular optimization is determined using Km (a known rate constant) and $V_{MAX}$ (maximum velocity) calculations. The assay compound is preferably present in an amount from about 2 to about 100×$V_{MAX}$ and most preferably from about 2 to about 10 times the amount which can be completely hydrolyzed by the enzyme within the duration of the assay period.

The assay may be conducted either as a rate determination or as an end point determination. Rate determinations are preferred, because they are generally less affected by autofluorescence. Consequently, a rate determination assay is more sensitive and precise. In a rate determination, the fluorescence of the assay compound-cell analyte mixture may be determined promptly after the cell analyte is contacted with the assay compound. The ability to see a signal and distinguish it from background noise determines the initial starting point of data collection and the final data point is preferably determined at the point where the slope of the reaction rate changes, typically more than 2%.

Most cellular reactions do not strictly obey zero-order kinetics. Most cellular enzymes show a delay between the time of exposure of the cells to the assay compound, and the ability to detect a signal that is greater than the background noise. Cellular enzymatic reactions that do not obey zero order kinetics are still useful measurements as first order, pseudo first order, or initial rate measurements. Multiple enzymes in a reaction (mixed reactions) are displayed by slope changes during the time course being monitored.

In an endpoint determination, the enzyme hydrolysis reaction is allowed to proceed for a predetermined length of time, usually at $V_{MAX}$. The reaction time can be calculated based on whether the reaction is zero order or first order kinetics using Michaelis-Menton methodology. Alternatively, the reaction time can also be adjusted by a different elapsed time for pseudo-first order reactions.

It has been determined that a number of factors will decrease the reliability of the assay, and yield false positive, or erroneous indications of enzymatic activity. These include (i) extended reaction between the cell analyte and the assay compound; (ii) another, non-targeted enzyme that is cleaving the leaving group; (iii) auto-hydrolysis of the assay compound; (iv) inhibitors or stimulators that are present and undetected; (v) cells that are no longer metabolically active, or dead; (vi) mixed populations of cells; (vii) a transfusion of the patient before sampling; (viii) non-specific dye uptake by negative cells; and (ix) background fluorescence. The creation of false negatives, or false indications of a lack of enzymatic activity, can be caused by (i) insufficient reaction between the cell analyte and the assay compound, (ii) a hypoosmotic media leading to a decrease in cell activity; (iii) a cell that is no longer metabolically active; (iv) burst cells; and (v) the presence of inhibitors to the target enzyme.

It has been further determined that assays will be significantly improved if reaction conditions are adjusted to maximize the activity of the assayed enzyme relative to other non-assayed enzymes which might otherwise compete for the leaving group. More specifically, the targeted enzyme can be involved in a chain cascade reaction of enzymes sequentially coupled to other enzymes, as in a multi-enzyme reaction cascade.

A reaction run using the same data collection window without the enzyme source will determine auto-hydrolysis of the substrate and therefore the potential for negative cells to absorb the dye non-specifically resulting in false positive.

The time of the assay is typically less than 30 minutes, preferably less than 20 minutes, usually between 5 seconds and 20 minutes, and most preferably between about 10 seconds and about 5 minutes. Some enzyme systems, such as esterases, can react with the assay compound in shorter periods of time due to concentrations of enzymes found in the cell. The reaction time should be limited so that the effects of cellular expulsion of the indicator compound will be avoided.

The temperature at which the assay is performed must be physiologically acceptable to the cell. The temperature must be high enough to retain viability and to ensure enzyme activity, but not so high as to cause degradation or other deleterious reactions involving the leaving group, the enzyme, or other components of the mixture. Particular enzymes, or enzymes in particular pathways, are more reactive at particular temperatures. The temperature is preferably maintained between about 30° C. to about 40° C., more preferably between about 35° C. and about 38° C., and most preferably between about 36° C. to about 38° C.

The osmotic pressure of the assay mixture is controlled to be within physiological ranges from about 250 milliosmoles to 350 milliosmoles, preferably from about 275 milliosmoles to 320 milliosmoles. The osmotic pressure must be selected to maintain the viability of the metabolically active whole cell. Variations in osmotic pressures will result in lysis of the cell, severe shrinking or shriveling (crenation) when too low, and swelling or bursting (stomatolysing) of the cell when too high.

The fluorescence reading is made after the reaction has occurred or after a specific period of time. Typically, the reaction is stopped by immersing the reaction container in ice and water which cools the cells to about 0° C. Sensing for one or more reaction states by fluorescence determinations confirms cleavage of the indicator group by the enzyme.

The fluorescence determinations can be performed on a Image Analysis System (IAS) or a Flow Cytometer (FC) or such other instruments which are capable of fluorescence determinations. The IAS is a microscope based system that measures fluorescence known to those skilled in the art. A representative example of an IAS is the Metamorph™ by Universal Imaging Corporation, West Chester, Pa. The structure and operation of flow cytometers is also well documented in the literature. Alternatives to traditional FC include slit-scan FC and stopped-flow FC. The type of instrument used to conduct the experiments described in the examples was a flow cytometer (for example, a Coulter Profile® flow cytometer manufactured by Coulter Corporation of Miami, Fla.). This flow cytometer measures fluorescence across the entire cell. Flow cytometric methods which measure fluorescence in only a part of the cell, such as slit scan flow cytometry, have significant utility in the invention because the background fluorescence is significantly reduced when measurements are focused on the region of the cell where the enzyme is located.

The fluorescence determinations can also be taken by a spectrofluorometer which has the capability to measure the very low fluorescence levels that are generated by the assay. The spectrofluorometer is tuned to the excitation and emission wavelengths of the particular indicator being used. Preferred compounds such as rhodamine 110 and fluorescein have excitation and emission wavelengths of about 495 to 498 nm (excitation) and 520 to 525 nm, respectively. The Model 8000C photon counting spectrofluorometer manufactured by the SLM company, a subsidiary of Milton Roy (Chicago, Ill.) was used.

The flow cytometer can perform additional measurements in addition to a single wavelength fluorescence measurement. The flow cytometers can be equipped to measure fluorescence at two or more separate wavelengths. Such readings are useful to perform assays according to the invention when using more than one assay compound, or for using cell surface markers, such as monoclonal antibodies, to determine cell phenotype.

VI. Assay Protocols

Preferred sample preparations by which enzymes can be assayed using the reagents prepared according to the method of the invention have been developed. Examples of these sample preparations can be modified, and are included herein to disclose those procedures that are currently preferred. Sample preparation can be divided into four different processes represented by Examples 5, 6, 7 and 8 which are illustrated in FIGS. 1A, 1B, 1C and 1D, respectively. The choice of sample preparation is dependent upon the user and the analyte. The four processes are:

EXAMPLE 5

Examination Of Leukocytes Or Tissue Cells With Erythrocyte Contamination With Post-Lysing A sample, consisting of whole blood (in EDTA, Heparin or ACD) or dissociated tissue or body fluids (synovial fluid) or cell culture media is obtained and stored in a manner so as not to decrease viability. The sample is washed sufficiently to remove plasma, media, body fluid, debris and extra-cellular enzymes. The wash media consists of a physiologically balanced buffered salt solution. The washed cells are incubated at 37° C. 50 $\mu$L of sample and 25 $\mu$L of substrate media are mixed together and allowed to incubate at 37° C. for a predetermined amount of time. At the end of the incubation period, unwanted cells are lysed with a lytic reagent, i.e., erythrocytes are removed. Compatible lytic systems are Q-Prep™, an acid lyse and a quench, Erythrolyse™ and Stabilyse™, or hypotonic ammonium chloride. The sample is then measured for fluorescence. The referenced lytic systems are commercially available from Coulter Corporation, Miami, Fla.

EXAMPLE 6

Examination Of Leukocytes Or Tissue Cells With Erythrocyte Contamination With Pre-Lysing A sample, consisting of whole blood (in EDTA, Heparin or ACD) or dissociated tissue or body fluids (synovial fluid) or cell culture media is obtained and stored in a manner so as not to decrease viability. Unwanted cells, i.e. erythrocytes, are lysed with a lytic reagent. Compatible lytic systems are acid lyse/quench, IVCS lyse (formic acid/ wetting agent/quench) or hypotonic ammonium chloride. The sample is washed sufficiently to remove plasma, media, body fluid, debris and extra-cellular enzymes. The wash media consists of a physiologically balanced buffered salt solution. The washed cells are incubated at 37° C. 50 $\mu$L of sample and 25 $\mu$L of substrate media are mixed together and allowed to incubate at 37° C. for a predetermined amount of time. At the end of the incubation period, the sample is then measured for fluorescence.

EXAMPLE 7

Examination Of Platelets, Erythrocytes, Leukocytes, Dissociated Tissue, Body Fluids And Cell Culture Media A sample, consisting of whole blood (in EDTA, Heparin or ACD) or dissociated tissue or body fluids (synovial fluid)

or cell culture media is obtained and stored in a manner so as not to decrease viability. The sample is washed sufficiently to remove plasma, media, body fluid, debris and extra-cellular enzymes. The wash media consists of a physiologically balanced buffered salt solution. The washed cells are incubated at 37° C. 50 μL of sample and 25 μL of substrate media are mixed together and allowed to incubate at 37° C. for a predetermined amount of time. At the end of the incubation period, the sample is then measured for fluorescence.

EXAMPLE 8

Examination Of Platelets, Erythrocytes, Leukocytes, Dissociated Tissue, Body Fluids And Cell Culture Media Using A Mechanical Separation To Isolate A Cell Population A sample, consisting of whole blood (in EDTA, Heparin or ACD) or dissociated tissue or body fluids (synovial fluid) or cell culture media is obtained and stored in a manner so as not to decrease viability. A mechanical separation to isolate a specific cell population is performed, i.e., ficoll, differential centrifugation, differential precipitation. The sample is washed sufficiently to remove plasma, media, body fluid, debris and extra-cellular enzymes. The wash media consists of a physiologically balanced buffered salt solution. The washed cells are incubated at 37° C. 50 μL of sample and 25 μL of substrate media are mixed together and allowed to incubate at 37° C. for a predetermined amount of time. At the end of the incubation period, the sample is then measured for fluorescence.

The instruments used to detect fluorescence are the flow cytometer or fluorescent microscope. There are four different instrument configurations for the flow cytometer, A, B, C and D. Any of the four configurations can be used with any one of the sample preparations described above. The choice of which configuration is selected is dependent upon the user and the information sought to be obtained. The four configurations are:

Configuration A:

Configuration A analyzes the cells by size, granularity and single color. In the first configuration, the flow cytometer separates the cells by size and granularity. The activity of an enzyme is then assayed using the reagent compound. Two samples are allowed to proceed at different times and the reaction is stopped. The difference in fluorescence permits the calculation of a rate. Total population counts preferred are 500 to 500,000 cells. Use of light scatter or hematology parameters provide size and granularity separation. Intensity bitmap of desired populations and determination of fluorescent activity by single measurement point or multi-point measurement can be employed. Determine count, percentage and fluorescent intensity of a multi-modal population representing enzymatic activity.

Configuration B:

Configuration B analyzes the cells by size, granularity and two colors. In the second configuration, the flow cytometer separates the cells by size and granularity. Cell morphology is determined by a fluorescence assay with a monoclonal antibody marker. The rate of the hydrolysis of the assay compound is then determined. Total population counts preferred are 500 to 500,000 cells. Use of light scatter or hematology parameters provide size and granularity separation. Intensity bitmap of desired populations and determination of fluorescent activity by single measurement or multi-point measurement can be employed. Determine count, percentage and fluorescent intensity of a multi-modal population representing enzymatic activity. The analysis is a 2-color analysis measuring enzymatic activity in one color and surface-marker antibody cell morphology in the other color.

Configuration C:

Configuration C analyzes the cells by size, granularity, two colors and backgate fluorescence. Configuration 3 is a modification of the Duque method. Duque, R. E., "Flow Cytometric Analysis of Lymphomas and Acute Leukemias", *Annals of the New York Academy of Sciences, Clinical Flow Cytometry*, 677, pp. 309–325 (Mar. 20, 1993). The size and granularity of the cell are separated by a flow cytometer using light scatter and/or with surface markers, such as monoclonal antibodies. A series of cell populations are determined, with rearrangement of the histogram to identify the disease and normal cells. The activity of the enzyme is then assayed. Total population counts preferred are 500 to 500,000 cells. Use of light scatter or hematology parameters provide size and granularity separation. Intensity bitmap of desired populations and determination of fluorescent activity by single measurement point or multi-point measurement can be employed. Determine count, percentage and fluorescent intensity of a multi-modal population representing enzymatic activity. The analysis is a 2-color analysis measuring enzymatic activity in one color and surface-marker antibody cell morphology in the other color. Backgate fluorescence data on size and granularity to determine count and percent of diseased cells.

Configuration D:

Configuration D analyzes activity of a population of cells over time. Total population counts preferred are 500 to 500,000. Use of light scatter or hematology parameters provide size and granularity separation. Intensity bitmap of desired populations and determination of fluorescent activity by single measurement point or multi-point measurement can be employed. Determine count, percentage and fluorescent intensity of a multi-modal population representing enzymatic activity. The analysis is a 2-color analysis measuring enzymatic activity in one color and surface-marker antibody cell morphology in the other color.

VII. Data Analysis

The measured fluorescence intensity can be converted from fluorescence mean channel (in peak or integrated mode) to MESF (molecules of equivalent soluble fluorochrome, Flow Cytometry Standards Corp., San Juan, Puerto Rico) or International Units of hydrolysis per cell.

The following detailed Examples are intended to illustrate this invention, but not limit its scope.

EXAMPLE 9

Method and Reagents for Measurement of Early Apoptosis Events in Jurkat Cells 1. The human T cell line, Jurkat, was maintained in RPMI 1640 medium supplemented with 10% fetal bovine serum.
2. To induce apoptosis, cells were washed once in sterile PBS, then resuspended in serum-free media at $1.0 \times 10^6$ cells/mL.
3. Purified CD95 (Coulter Corporation, clone 7C11) was added to cells at a concentration of 1.0 μg/$1.0 \times 10^6$ cells.
4. Cells were returned to the humidified incubator at 37° C. in 5% $CO_2$. After 15 minutes, one, two and one half, or four hours of incubation, a sample was removed for analysis. The cells were centrifuged and washed once in warm Hanks' buffer, pH 7.5. The final count was adjusted to 3.0+/−0.5×10$^6$ cells/mL.

5. The assay was performed as follows: Pipette 50 μL of washed cells from step 4 into a labeled test tube. Pre-warm the samples in a 37° C. water bath for 5 to 10 minutes. While samples are warming, prepare the assay reagents to be used by reconstituting each vial with 0.250 mL of pyrogen-free water.
6. Add 25 μL of the appropriate assay reagent to each test tube. Mix gently by hand. Incubate for exactly one, five, or ten minutes depending on the reagent used. See package insert for exact timings. Place the test tubes on crushed ice for at least three minutes, but not longer than 20 minutes.
7. Add 500 μL of ice cold Hanks' buffer to each tube before analyzing on the flow cytometer. Samples must be analyzed within 30 minutes of the 37° C. incubation.

Apoptosis involves a cascade of specific biochemical events. A reagent of this invention comprising (SEQ ID NO:1)$_2$ Rho 110·2TFA is designed to measure the activity of the enzyme apopain (CPP32, YAMA). This enzyme is known to be involved in apoptosis, cleaving poly-ADP Ribose Polymerase (PARP). The mean channel fluorescence for (SEQ ID NO:1)$_2$ Rho 110·2TFA increases after about 15 minutes and continues to increase throughout the four-hour testing period.

Figure 3:
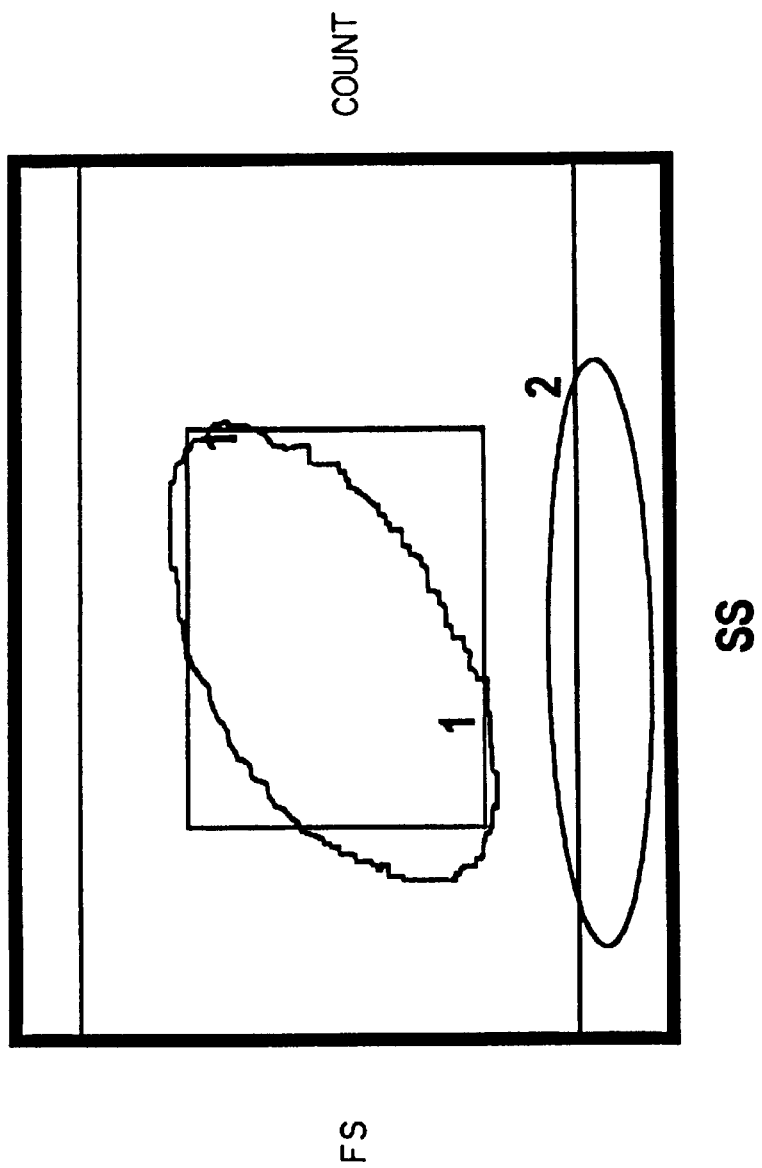
FIG. 3 is a scattergram differentiating live cells and dead cells which have been apoptically stimulated.

Results for the Jurkat cell enzyme levels are represented by mean channel fluorescence values. With time, bimodal populations are seen in FIG. 3 which is a scattergram of forward angle light scatter versus side angle light scatter. Inclusion of all event in the scattergram enables live cells, dead cells and cell debri to be analyzed. Reducing the number of events by bitmapping further enables one to obtain a distinct population of live cells and dead cells. Bimodal populations within a live cell bitmap represent the proportion of cells activated in apoptosis.

More specifically, the bimodal populations appear to represent cells that have been induced to undergo apoptosis, as well as cells that are have undergone apoptosis induced by the CD95 antibody. CD95 is a member of the Nerve Growth Factor Receptor/Tumor Necrosis Factor family. The CD95 antigen, also known as Fas or APO-1, is a cell surface molecule that mediates apoptosis.

The results demonstrate in FIG. 4 that the reagents of this invention can be used to detect apoptotic activity as early as 15 minutes after apoptosis was induced in Jurkat cells using CD95 antibody. By four hours after induction of apoptosis, these enzyme levels are decreasing, possibly because these enzymes have performed their function in cell death and are returning to native levels. Comparisons are shown in Table 1.

(Asp)$_2$ Rho110·2TFA shows a similar pattern to (SEQ ID NO:1)$_2$ Rho 110·2TFA. This may be due to the cleavage position at Asp (aspartic acid) in the caspase family. The (Leu Leu)$_2$ Rho110·2TFA increase may be due to its involvement in activating granzymes by cleaving the pro-granzyme form.

Further embodiments of the reagent of this invention comprising (SEQ ID NO:3)$_2$ Rho110·2TFA which is designed to measure the activity of the enzyme granzyme B and (SEQ ID NO:5)$_2$ Rho110·2TFA which is designed to measure the activity of the enzyme for granzyme A.

The cells undergoing apoptosis form extra-cellular "blebs" of cellular material which, when analyzed by flow cytometry, results in bimodal peaks of enzyme activity. This occurs in the live cell bitmap and the dead cell bitmap.

TABLE 1

COMPARISON OF ENZYMES ASSOCIATED IN JURKAT CELL APOPTOSIS WITH ENZYMES IN AN INFLAMATORY NECROTIC RESPONSE

| Reagent | Control | 15 Min. | 1 Hr. | 2.5 Hr. | 4 Hr. |
| --- | --- | --- | --- | --- | --- |
| Reagent A | 266.6 | 260.5 | 338.3 | 345.3 | 169.0 |
| Reagent B | 0.415 | 0.485 | 0.697 | 0.840 | 0.767 |
| Reagent C | 17.68 | 20.43 | 18.66 | 32.48 | 51.84 |
| Reagent D | 11.40 | 22.82 | 69.37 | 102.6 | 75.98 |
| Reagent E | 17.47 | 17.29 | 9.204 | 9.792 | 7.174 |
| Reagent F | 1.448 | 1.514 | 2.113 | 3.257 | 4.163 |

Reagent A = Fluorescein dichloroacetate
Reagent B = (Asp)$_2$ Rho 110.2TFA
Reagent C = (Leu Leu)$_2$ Rho 110.2TFA
Reagent D = (Val Lys)$_2$ Rho 110.2TFA
Reagent E = (Phe Arg)$_2$ Rho 11.2TFA
Reagent F = (SEQ ID NO:1)$_2$ Rho 110.2TFA Reagent A, D and E are typically elevated in an inflamatory response. In the above study, the initial response is towards elevation but then all enzymatic activity is decreased. The comparison between cellular enzymes found in a necrotic condition show elevated tendencies. On the other hand, Reagent B, C and F are typically elevated only at the four hour period in an apoptosis event and gradually diminish over an 18 hour period. Thus one can determine the difference between necrosis and apoptosis by monitoring the extended reaction which will depict the necrosis enzyme activity as increasing and the apoptotic enzyme activity as decrease after an initial increase. It has also been determined that other enzymes can exhibit similar patterns to distinguish between apoptotic and necrotic events.

EXAMPLE 10

METHOD OF DETERMINING APOPTOTIC STAGE IN APOPTOTIC CASCADE FOR CASPACE AND CALPAIN ENZYMES

Cysteine protesases are involved in the apoptosis pathway, and their activity increases during apoptosis. A peptide analog of the inhibitor for CPP32 which is a cysteine protease is acetyl-Asp-Glu-Val-Asp-aldehyde (ac-(SEQ ID NO:1).CHO). Another peptide anlog of the inhibitor for ICE, which is also a cysteine protease, is acetyl-Tyr-Val-Ala-Asp-aldehyde (ac-(SEQ ID NO:2).CHO).

Calcium activation occurs as a separate event in apoptosis outside of the Caspase enzyme pathway. Calpain enzyme is activated by the calcium activation which can further cause degranulation in the cell.

Reagents of this invention have been developed having the formula of (SEQ ID NO:1)$_2$-Rho 110·2TFA and (SEQ ID NO:2)$_2$-Rho 110·2TFA and (SEQ ID NO:6)$_2$Rho100·2TFA. It has been found that (SEQ ID NO:6)$_2$Rho110·2TFA cross reacts with dipeptidyl peptidase I enzyme and therefore should include an inhibitor for such enzyme, such as N-ethyl maleimide.

The human histiocytic lymphoma U937 cell line was induced to undergo apoptosis by the addition of camptothecin. CPP32 inhibitor, ac-(SEQ ID NO:1).CHO and ac-(SEQ ID NO:2).CHO, were added before the cells were stimulated to undergo apoptosis. It was expected that the inhibitors would reduce the enzymatic activity of the cysteine protease. The effects of the inhibitor on the cell line was measured using the reagents of this invention in the following method. The calpain enzyme activity was separately monitored concurrent with the inhibitor study.

1. The human histiocytic lymphoma U937 cell line was maintained in RPMI-1640 medium (Biowhittaker) supplemented with 10% fetal bovine serum (Biowhittaker), 50 units/mL penicillin and 50 μg/mL streptomycin (Life Technologies). The cells were maintained in a humidified incubator at 37° C. in 5% $CO_2$.

2. CPP32 Inhibitor, Ac-Asp-Glu-Val-aspartic acid aldehyde and IL-1β Converting Enzyme (ICE) Inhibitor I (Ac-Tyr-Val-Ala-aspartic acid aldehyde), were purchased from Sachem. They were prepared as 10 mM stocks in medium RPMI-1640 supplemented with 10% fetal bovine serum, 50 units/mL penicillin and 50 μg/mL streptomycin. U937 cells, 0.8 to $1.0 \times 10^6$ cells/mL, to be used for the day's experiments were aliquoted into 25 cm2 tissue culture flasks, approximately eight mL per flask. The appropriate inhibitor was added at time zero to give a final concentration of inhibitor of 300 μmoles. All flasks were returned to the incubator for one hour.

3. Camptothecin (Calbiochem) was prepared as a 4 mg/mL stock solution in DMSO. U937 cells were induced to undergo apoptosis by the addition of 4 μg/mL of camptothecin using the stock solution. Cells were incubated in the $CO_2$ incubator for the times indicated. The control and calpain samples represent cells in the initial preparation with no added inhibitor or camptothecin.

4. After one, three, or four hours incubation, the cells were centrifuged and washed once in warm (37° C.) Hanks' buffer, pH 7.5. The final count was adjusted to $3.0 \pm 0.5 \times 10^6$ cells/mL.

5. The assay was performed in multiple aliquots of cells using the substrates (SEQ ID NO: 1)$_2$-Rho 110·2TFA and (SEQ ID NO:2)$_2$-Rho 110·2TFA and (SEQ ID NO:6)$_2$Rho110·2TFA. Pipet 50 μl of washed cells from step 4 to a labeled test tube. Prewarm the samples in a 37° C. water bath for 5 to 10 minutes. While the samples are warming prepare the substrates by reconstituting a vial with 0.250 mL of pyrogen-free water.

6. Add 25 μl of each substrate to each test tube. Mix gently by hand. Incubate for exactly 10 minutes at 37° C. Place the test tubes on crushed ice for at least three (3) minutes, but not longer than 20 minutes.

7. Add 500 μl of ice cold Hanks' buffer to each tube before analyzing on the flow cytometer. Samples must be analyzed within 30 minutes of 37° C. incubation.

TABLE 2

CALPAIN ENZYMATIC ACTIVITY

|  | Calpain | Blank |
| --- | --- | --- |
| Control | 1.309 | 1.141 |
| 1 Hr. | 117.6 |  |
| 3 Hr. | 94.31 |  |
| 4 Hr. | 65.33 |  |

The results for the U937 cell line CPP32 and ICE enzyme levels are shown in mean channel fluorescence values in FIG. 6. The results demonstrate that the (SEQ ID NO:1)$_2$Rho110·2TFA is a specific substrate for the enzyme CPP32 or apopain.

When the peptide inhibitor ac-(SEQ ID NO:1)·CHO is added before the induction of apoptosis, the reaction is inibihited. When ac-(SEQ ID NO:2)·CHO, the peptide inhibitor of interleukin-1β-converting enzyme (ICE), is added to the cell line, CPP32 activity is also inhibited.

These results indicate that the production of CPP32-like activity during apoptosis depends on the previous activation of interleukin-1β-converting enzyme (ICE).

When ac-(SEQ ID NO:2)·CHO, the peptide inhibitor of interleukin-1β-converting enzyme (ICE), is added to the cell line, ICE activity is inhibited. When the peptide inhibitor ac-(SEQ ID NO:1)·CHO is added before the induction of apoptosis, the reaction is only diminished.

These results demonstrate that the substrate of this invention is specific for the target enzyme since it can be inhibited with known inhibitors. In addition, the results demonstrate the enzyme position in the apoptosis cascade for DNA damage.

These results also demonstrate that calpain enzymes have more than a 100 fold increase after 4 hours after calcium activation. This evidences that other cytoplasmic enzymes, not in the caspase enzyme pathway, are activated.

Apoptosis is part of the pathology of many viral infections, including infection with baculovirus, HIV, and influenza virus. If apoptosis is inhibited, the infection can persist, become latent, or viral production can be enhanced. This happens with adenovirus, HIV, and probably Epstein-Barr virus and herpes virus. Promotion of apoptosis increases virus spread and release. Several neurodegenerative diseases such as Alzheimer's disease, Huntington's disease, Parkinson's disease and amyotrophic lateral sclerosis (Lou Gehrig's disease) appear to be due to the progressive loss of brain neurons by apoptosis. Thus a direct connection between many disease states and apoptosis has been established.

All patents and publications referred to in this application are hereby incorporated by reference in their entirety.

The invention has been described with reference to the preferred embodiments. It should be understood, however, that the invention is not so limited, and the scope of the invention should be determined with reference to the following claims, rather than to the foregoing specification.

We claim:

1. An assay reagent for determining the activity of an enzyme in a metabolically active whole cell, said assay reagent comprising at least one water soluble physiologically acceptable salt having the ability to pass through a cell membrane, said assay compound having an unblocked leaving group selected for cleavage by an enzyme to be analyzed selected from cysteine protease, dipeptyl peptidase and calpain, and a fluorogenic indicator group being selected for its ability to have a non-fluorescent first state when joined to the leaving group, and a fluorescent second state excitable at a wavelength above 450 nm when the unblocked leaving group is cleaved from the indicator group by the enzyme, wherein said fluorogenic indicator group is selected from the group consisting of rhodamine 110, rhodol, fluorescein and derivative thereof, said assay reagent having a fluorescence less than the auto-fluorescence of a metabolically active cell.

2. The assay reagent of claim 1, wherein the enzyme is a caspase enzyme of cysteine proteases.

3. The assay reagent of claim 1, wherein the enzyme is a granzyme of cysteine proteases.

4. The assay reagent of claim 1 wherein said derivatives of the indicator group are selected from the group consisting of 4'(5')aminorhodamine 110, 4'(5')carboxyrhodamine 110, 4'(5')chlororhodamine 110, 4'(5')methylrhodamine 110, 4'(5')sulforhodamine 110, 4'(5')aminorhodol, 4'(5') carboxyrhodol, 4'(5')chlororhodol, 4'(5')methylrhodol, 4'(5') sulforhodol, 4'(5')aminofluorescein, 4'(5') carboxyfluorescein, 4'(5')chlorofluorescein, 4'(5') methylfluorescein, and 4'(5')sulfofluorescein.

5. The assay reagent of claim 1, wherein said unblocked leaving group has an amino acid sequence selected from YVAD, DEVD, VEID, AAD, LY and PFR.

6. The assay reagent of claim 5, wherein said physiologically acceptable salt is an acid salt.

7. The assay reagent of claim 6, wherein said acid salt is a trifluoroacetic acid salt.

8. The assay reagent of claim 7, wherein said assay reagent fails to detect a target enzyme which has been inhibited.

9. The assay reagent of claim 8, wherein said target enzyme is selected from cysteine protease, dipeptyl peptidase and calpain.

10. A method of performing an assay for detecting the presence of a enzymatic activity in a metabolically active whole cell to determine the apoptotic stage of the cell comprising:

(a) contacting a test, metabolically active whole cell with an assay reagent, said assay reagent comprising at least one water soluble physiologically acceptable salt having the ability to pass through a cell membrane, said assay compound having an unblocked leaving group selected for cleavage by an enzyme to be analyzed selected from cysteine protease, dipeptyl peptidase and calpain, and a fluorogenic indicator group being selected for its ability to have a non-fluorescent first state when joined to the leaving group, and a fluorescent second state excitable at a wavelength above 450 nm when the unblocked leaving group is cleaved from the indicator group by the enzyme, wherein said fluorogenic indicator group is selected from the group consisting of rhodamine 110, rhodol, fluorescein and derivative thereof; said assay reagent having a fluorescence less than the auto-fluorescence of a metabolically active cell, (b) sensing for said fluorescent second state of the indicator group for the test, metabolically active whole cell to produce a test result, and (c) determining an apoptotic stage of said metabolically active whole cell from said test result.

11. The method of claim 10 wherein the enzyme is a caspase enzyme of cysteine proteases.

12. The method of claim 10 wherein the enzyme is a granzyme of cysteine proteases.

13. The method of claim 10 wherein said derivatives of the indicator group are selected from the group consisting of 4'(5')aminorhodamine 110, 4'(5')carboxyrhodamine 110, 4'(5')chlororhodamine 110, 4'(5')methylrhodamine 110, 4'(5')sulforhodamine 110, 4'(5')aminorhodol, 4'(5') carboxyrhodol, 4'(5')chlororhodol, 4'(5')methylrhodol, 4'(5') sulforhodol, 4'(5')aminofluorescein, 4'(5') carboxyfluorescein, 4'(5')chlorofluorescein, 4'(5') methylfluorescein, and 4'(5')sulfofluorescein.

14. The method of claim 10 wherein said unblocked leaving group has an amino acid sequence selected from YVAD, DEVD, VEID, AAD, LY and PFR.

15. The method of claim 14 wherein said physiologically acceptable salt is an acid salt.

16. The method of claim 15 wherein said acid salt is a trifluoroacetic acid salt.

17. The method of claim 16 wherein said assay reagent fails to detect a target enzyme which has been inhibited.

18. The method of claim 17 wherein said target enzyme is selected from cysteine protease, dipeptyl peptidase and calpain.

19. The method of claim 10 which further comprises differentiating an apoptotic stage of said metabolically active whole cell from necrosis of said metabolically active whole cell.

20. The method of claim 19 wherein said apoptotic stage exhibits a deceased caspase enzyme activity and necrosis exhibits an increased calpain enzyme activity.

\* \* \* \* \*

SEQUENCE LISTING (1) GENERAL INFORMATION:

(iii) NUMBER OF SEQUENCES: 6

(2) INFORMATION FOR SEQ ID NO:1:

```
        (i) SEQUENCE CHARACTERISTICS:
            (A) LENGTH: 4 amino acids
            (B) TYPE: amino acid
            (C) STRANDEDNESS:  single
            (D) TOPOLOGY: linear (ii) MOLECULE TYPE: Peptide (xi) SEQUENCE DESCRIPTION: SEQ ID NO: 1:

Asp Glu Val Asp
1

(2) INFORMATION FOR SEQ ID NO:2:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:2:

Tyr Val Ala Asp
1

(2) INFORMATION FOR SEQ ID NO:3:

(i) SEQUENCE CHARACTERISTICS:
            (A) LENGTH: 3 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Ala Ala Asp
1

(2) INFORMATION FOR SEQ ID NO:4:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (ix) SEQUENCE DESCRIPTION: SEQ ID NO:4:

Val Glu Ile Asp
1

(2) INFORMATION FOR SEQ ID NO:5:

(i) SEQUENCE CHARACTERISTICS:
            (A) LENGTH: 3 amino acids
            (B) TYPE: amino acid
            (C) STRANDEDNESS: single
            (D) TOPOLOGY: linear (ii) MOLECULE TYPE: peptide (ix) SEQUENCE DESCRIPTION: SEQ ID NO:5:

Pro Phe Arg
1

(2) INFORMATION FOR SEQ ID NO:6:
```

-continued

```
    (i) SEQUENCE CHARACTERISTICS:
        (A) LENGTH: 2 amino acids
        (B) TYPE: amino acid
        (C) STRANDEDNESS: single
        (D) TOPOLOGY: linear (ii) MOLECULE TYPE: peptide (ix) SEQUENCE DESCRIPTION: SEQ ID NO:6:

Leu Tyr
```